United States Patent [19]

Rüttimann

[11] Patent Number: 4,663,470

[45] Date of Patent: May 5, 1987

[54] ALPHA-TOCOPHEROL INTERMEDIATES

[75] Inventor: August Rüttimann, Arlesheim, Switzerland

[73] Assignee: Hoffman-La Roche Inc., Nutley, N.J.

[21] Appl. No.: 919,729

[22] Filed: Oct. 16, 1986

Related U.S. Application Data

[62] Division of Ser. No. 777,125, Sep. 18, 1985, Pat. No. 4,642,361.

[30] Foreign Application Priority Data

Oct. 11, 1984 [CH] Switzerland ............... 4871/84

[51] Int. Cl.⁴ .......................................... C07D 303/32
[52] U.S. Cl. ..................................................... 549/544
[58] Field of Search ........................................ 546/544

[56] References Cited

U.S. PATENT DOCUMENTS 3,657,287  4/1972  Kawamatsu et al.
4,603,223  7/1986  Ruttimann et al.

FOREIGN PATENT DOCUMENTS 107738   5/1984  European Pat. Off.
1587741  4/1981  United Kingdom.

Primary Examiner—Norma S. Milestone
Attorney, Agent, or Firm—Jon S. Saxe; Bernard S. Leon; George W. Johnston

[57] ABSTRACT

A novel process for the manufacture of quinone derivatives which are suitable as intermediates for the manufacture of (2RS,4′R,8′R)-tocopherol is described. In this process a quinone of the formula

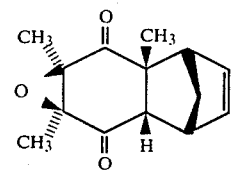

is reacted with a phytyl derivative of the formula

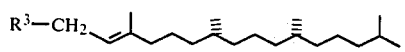

If desired, the thus-obtained compound of the formula

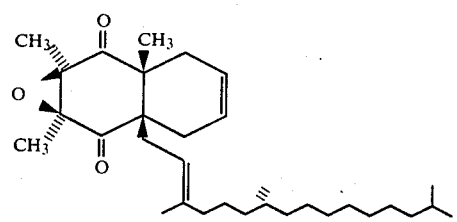

is subsequently converted into the compound of the formula

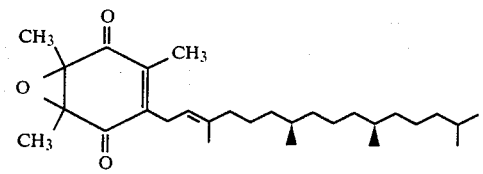

and, if desired, this compound is converted into the compound of the formula

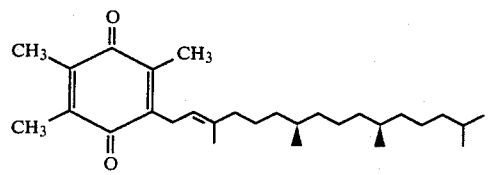

The compound of formula V is known and can be converted into (2RS,4′R,8′R)-tocopherol in a known manner.

1 Claim, No Drawings

ALPHA-TOCOPHEROL INTERMEDIATES

This is a division of application Ser. No. 777,125 filed Sept. 18, 1985, now U.S. Pat. No. 4,642,361.

BACKGROUND OF THE INVENTION

The present invention is concerned with a novel process for the manufacture of quinone derivatives which are suitable as intermediates for the manufacture of (2RS,4′R,8′R)-tocopherol. The invention is also concerned with a novel starting material and novel intermediates in this process.

SUMMARY OF THE INVENTION

The process in accordance with the invention comprises reacting a compound of the formula

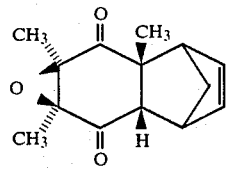

with a compound of the formula

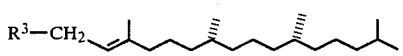

wherein $R^3$ represents a leaving group, if desired, converting the thus-obtained compound of the formula

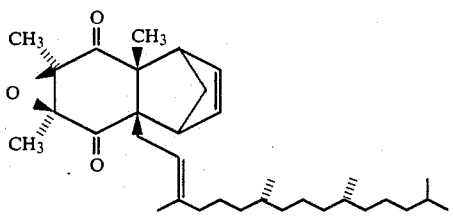

into the compound of the formula

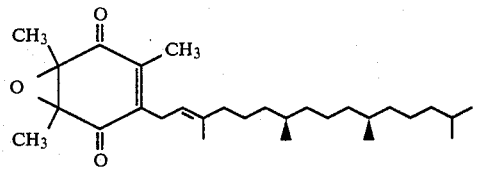

and, if desired, converting the thus-obtained compound of formula IV into the compound of the formula

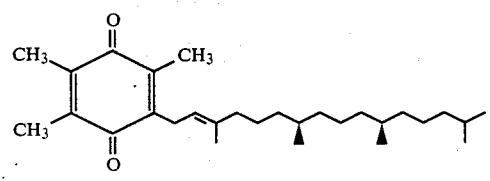

DETAILED DESCRIPTION OF THE INVENTION

The process in accordance with the invention comprises reacting a compound of the formula

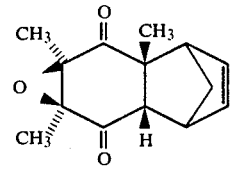

with a compound of the formula

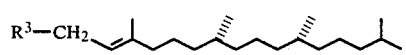

wherein $R^3$ represents a leaving group to produce a compound of the formula

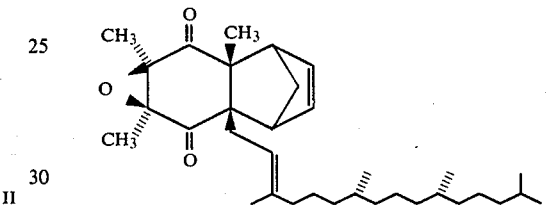

Compound III can be converted into a compound of the formula

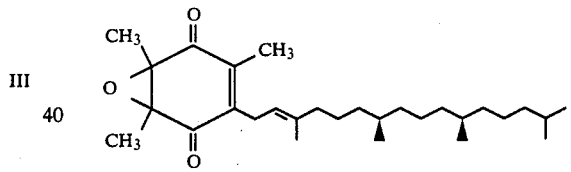

If desired, compound IV can be converted into a compound of the formula

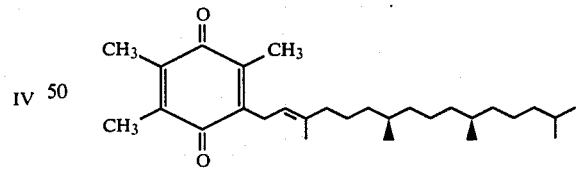

Compound V is an known intermediate in a known process for the manufacture of (2RS,4′R,8′R)-tocopherol.

The term "leaving group" signifies in the scope of the present invention any conventional group which can be cleaved off under conventional conditions. The term signifies especially halogen such as fluorine, chlorine, bromine and iodine, with bromine and chlorine being preferred, as well as groups such as the mesyl group, the tosyl group, the acetate group and the like. Furthermore, the notation "▼" signifies that the corresponding residue is situated above the plane of the molecule and the notation "|| || ||" signifies that the corresponding residue is situated below the plane of the molecule.

The term "alkyl" denotes straight or branched chain alkyl groups of 1 to 12 carbon atoms. Exemplary alkyl groups are methyl, ethyl, isobutyl, hexyl and the like.

The term "alkali metal" denotes lithium, sodium and potassium.

The compounds of formulae I, III and IV are novel and are also objects of the present invention.

The reaction of the compound of formula I with a compound of formula II can be carried out in an organic solvent which is inert under the reaction conditions and in the presence of any conventional strong base. Not only any conventional polar solvents, but also any conventional apolar solvents come into consideration as the solvent. There are preferred apolar aprotic solvents such as e.g. aliphatic or aromatic hydrocarbons such as hexane, benzene, toluene and the like and tert.butanol as the polar protic solvent. Mixtures of these solvents are also preferred. As strong bases there especially come into consideration in the scope of the present invention organic bases such as e.g. amides such as alkali metal amides (Li, Na, K) or lithium dialkylamides, alcoholates such as alkali metal tert.butylates as well as hydrides such as sodium hydride or potassium hydride and the like. Further, the reaction can be carried out at a temperature of about −70° C. to about +50° C., preferably at about 0° C. to about −30° C. and especially at about room temperature.

The conversion of the compound of formula III into the compound of formula IV represents a retro Diels-Alder reaction and can be carried out in a manner known per se. The heating can be carried out in the absence or in the presence of an inert solvent, for example at a temperature of about 140° C. to about 200° C., preferably at a temperature of about 150° C. to about 170° C.

The conversion of the compound of formula IV into the compound of formula V can be carried out in a manner known per se. This is conveniently carried out by the reductive cleavage of the epoxy group. Especially suitable reduction agents are zinc in acetic acid, zinc amalgam in acetic acid, sodium bisulphite, lithium in diethylamine and the like. Preferred reduction systems are zinc or zinc amalgam in acetic acid. As the carbonyl groups are also reduced in this reduction, the hydroquinone which is thereby obtained must subsequently be oxidized. This oxidation can also be carried out in a manner known per se. As oxidation agents there can be used oxygen, air, aqueous KOCl or NaOCl solutions, alkali metal chromates and the like, with oxygen (air) and aqueous KOCl or NaOCl solutions being especially suitable.

The compound of formula V is known and can be converted into (2RS,4′R,8′R)-tocopherol in a known manner. For example, this conversion can be carried out according to Isler, O. et. al., Vitamins and Hormones, 20, 389 (1962).

The compound of formula I which is used as the starting material in the process in accordance with the invention is novel. However, it can be obtained readily in a manner known per se by epoxidizing the compound of the formula

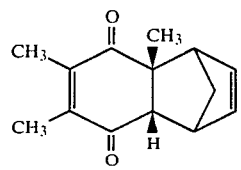

This epoxidation is conveniently carried out with 30% $H_2O_2$ in a lower alcohol with 1 to 4 carbon atoms in the pressure of a base such as e.g. alkali metal and alkaline earth metal carbonates or hydroxides at a temperature of about room temperature to about the reflux temperature of the reaction mixture, preferably at about 50° to 70° C.

The following Examples illustrate the invention. Unless otherwise stated, percentages and ratios are expressed in volume, temperatures are in degrees Celsius (°C.) and room temperature is about 21°–25° C. Unless otherwise indicated, the Examples were carried out as written.

EXAMPLE 1

180 ml of a mixture of tert.butanol/toluene (4:1) and 9.6 g (0.25 mol) of potassium were placed under argon in a 350 ml sulphonation flask provided with a stirrer, a reflux condenser and argon gasification and heated at reflux for 2 hours. Thereupon, the mixture was cooled to −3° C. by means of an ice-bath and treated with 26.6 g (0.112 mol) of (1aRS,2aRS,3SR,6RS,6aSR,7aSR)-1a,-2a,3,6, 6a,7a-hexahydro-1a,2a,7a-trimethyl-3,6-methanooxireno[b]-naphthalene-2,7-dione. Thereafter, 56.5 g (0.157 mol) of (2E,7R,11R)-phytylbromide in 80 ml of tert.butanol/toluene (4:1) were added dropwise at +5° C. within 30 minutes and the mixture was stirred at room temperature for a further 30 minutes. Subsequently, 20 ml of water were added and the mixture was concentrated at 30° C. on a rotary evaporator. The residue was taken up twice in 500 ml of hexane each time, washed twice and semisaturated NaCl solution and subsequently dried over $Na_2SO_4$. There were obtained 68.3 g of a brown crude product. Therefrom there were obtained by chromatography on silica gel with hexane/ether (97:3) 40.2 g of (1aRS,2aRS,3SR,-6RS,6aSR,7aSR)-1a,2a,3,6,6a,7a-hexahydro-1a,6a,7a-trimethyl-2a-[(E,7R,11R)-3,7,11,15-tetramethyl-2-hexadecenyl]-3,6-methanooxireno[b]naphthalene-2,7-dione as a pale yellow oil with a HPLC content of 99%.

The (1aRS,2aRS,3SR,6RS,6aSR,7aSR)-1a,2a,3,6,6a,-7a-hexahydro-1a,2a,7a-trimethyl-3,6-methanooxireno[b]naphthalene-2,7-dione used as the starting material was prepared as follows:

143.1 g (0.663 mol) of 1,4,4a,8aα-tetrahydro-4aα,6,7-trimethyl-1α,4α-methanonaphthalene-5,8-dione were dissolved in 1.1 liter of ethanol at 50° C. under argon in a 2.5 liter sulphonation flask provided with a stirrer, a reflux condenser and argon gasification. A solution of 23 g (0.3 eg.) of $Na_2CO_3$ in 500 ml of water and 115 ml (1.5 eg.) of 30% $H_2O_2$ was then added dropwise at 50° C. during 1.5 hours and the mixture was stirred at 50° C. for 30 minutes. The mixture was subsequently cooled to room temperature, extracted three times with 1 liter of ether each time, washed with water, dilute $NaHCO_3$ solution and saturated NaCl solution, then dried and concentrated. There were obtained 165.7 g of white crystals. After recrystallization from methanol there were obtained 146.6 g of (1aRS,2aRS,3SR,6RS,6aSR- ,7aSR)-1a,2a,3,6,6a,7a-hexahydro-1a,2a,7a-trimethyl-3,6-methanooxireno[b]-naphthalene-2,7-dione with a melting point of 72°–73° C.

EXAMPLE 2

40.2 g (78.6 mmol) of (1aRS,2aRS,3SR,6RS,6aSR,7aSR)-1a,2a,3,6,6a,7a-hexahydro-1a,6a,7a-trimethyl-2a-[(E,7R,11R)-3,7,11,15-tetramethyl-2-hexadecenyl]-3,6-methanooxireno[b]naphthalene-2,7-dione (prepared in accordance with Example 1) were heated to 170° C. for 4 hours under argon in a 150 ml round flask. The mixture was thereupon cooled to room temperature and chromatographed on SiO2 with ethyl acetate/hexane (5:95). By concentration of the pure eluate there were obtained 34.1 g of (1SR,6RS)-1,4,6-trimethyl-3-[(E,7R,11R)-3,7,11,15-tetramethyl-2-hexadecenyl]-7-oxabicyclo[4.1.0]hept-3-ene-2,5-dione as a yellow oil with HPLC content of 99%.

EXAMPLE 3

34.1 g (76.8 mmol) of (1SR,6RS)-1,4,6-trimethyl-3-[(E,7R,11R)-3,7,11,15-tetramethyl-2-hexadecenyl]-7-oxabicyclo[4.1.0]hept-3-ene-2,5-dione (prepared in accordance with Example 2) were dissolved in 350 ml of acetic acid under argon in a 500 ml sulphonation flask provided with a stirrer, a reflux condenser and argon gasification and the solution was treated with 20.5 g of amalgamated zinc, whereby the mixture heated up. After stirring for 1.5 hours the mixture was extracted twice with 0.5 l of hexane. The combined extracts were washed with 3N HCl and then with saturated NaHCO3 solution. The hexane phase was then heated with 50 ml of 2N NaOH and oxygen was conducted through the mixture for 1 hour while stirring. The mixture was subsequently extracted twice with 0.5 l of hexane each time, the extracts were washed twice with 0.5 l of water each time, dried and concentrated at 40° C. in a water-jet vacuum.

There were obtained 32.8 g of crude product in the form of a yellow oil. After chromatography on SiO2 with ether/hexane (1:19) there were obtained 32.5 g of 2,5,6-trimethyl-3-[(E,7R,11R)-3,7,11,15-tetramethyl-2-hexadecenyl]-benzoquinone with a HPLC content of 99%.

I claim:
1. A compound of the formula

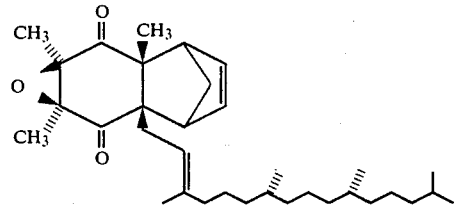

III